United States Patent [19]

Ohe et al.

[11] Patent Number: 4,643,566
[45] Date of Patent: Feb. 17, 1987

[54] PARTICLE ANALYZING APPARATUS

[75] Inventors: Shinichi Ohe, Machida; Yuji Ito, Chigasaki, both of Japan

[73] Assignee: Canon Kabushiki Kaisha, Tokyo, Japan

[21] Appl. No.: 753,871

[22] Filed: Jul. 11, 1985

[30] Foreign Application Priority Data

| Jul. 20, 1984 [JP] | Japan | 59-150641 |
| Jul. 20, 1984 [JP] | Japan | 59-150642 |
| Aug. 16, 1984 [JP] | Japan | 59-170832 |
| Nov. 27, 1984 [JP] | Japan | 59-250283 |

[51] Int. Cl.$^4$ .................. G01N 33/48; G01N 21/64
[52] U.S. Cl. ........................... 356/72; 356/317; 356/375
[58] Field of Search ............ 356/39, 72, 73, 317, 356/318, 375, 341; 250/461.2

[56] References Cited

U.S. PATENT DOCUMENTS

| 4,341,472 | 7/1982 | Gorog et al. | 356/375 |
| 4,510,438 | 4/1985 | Auer | 356/72 |
| 4,600,302 | 7/1986 | Sage | 356/39 |

Primary Examiner—R. A. Rosenberger
Attorney, Agent, or Firm—Fitzpatrick, Cella, Harper & Scinto

[57] ABSTRACT

A particle analyzing apparatus has a flow cell provided with a flow section passing therethrough a particle to be examined, an irradiating system for irradiating the particle to be examined in the flow cell with an irradiation light beam having a predetermined light intensity distribution in a direction perpendicular to the direction of application, a photodetector for photometering the light from the particle to be examined irradiated by the irradiating system, a detector for detecting the information regarding the light intensity of the irradiation light beam of the irradiating system at the position of the particle to be examined, and a compensation part for correcting the output of the photodetector on the basis of the output of the information detector.

9 Claims, 17 Drawing Figures

Fig. 13
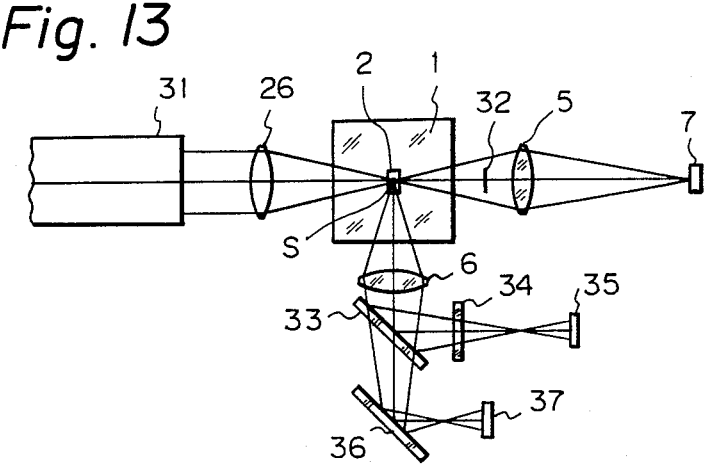
Fig. 14A
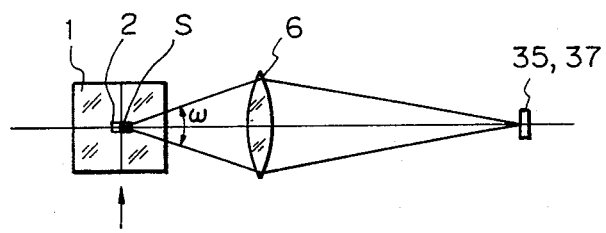
Fig. 14B
Fig. 14C
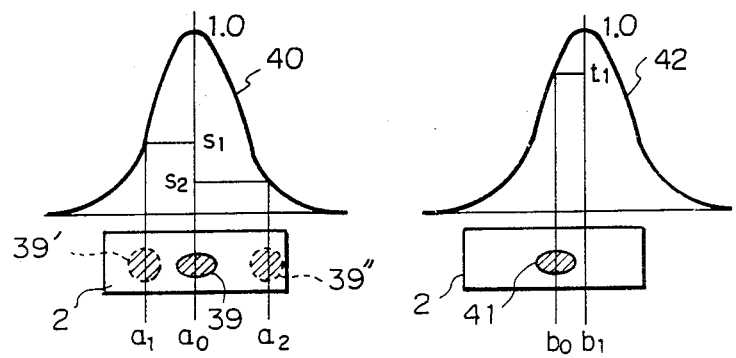

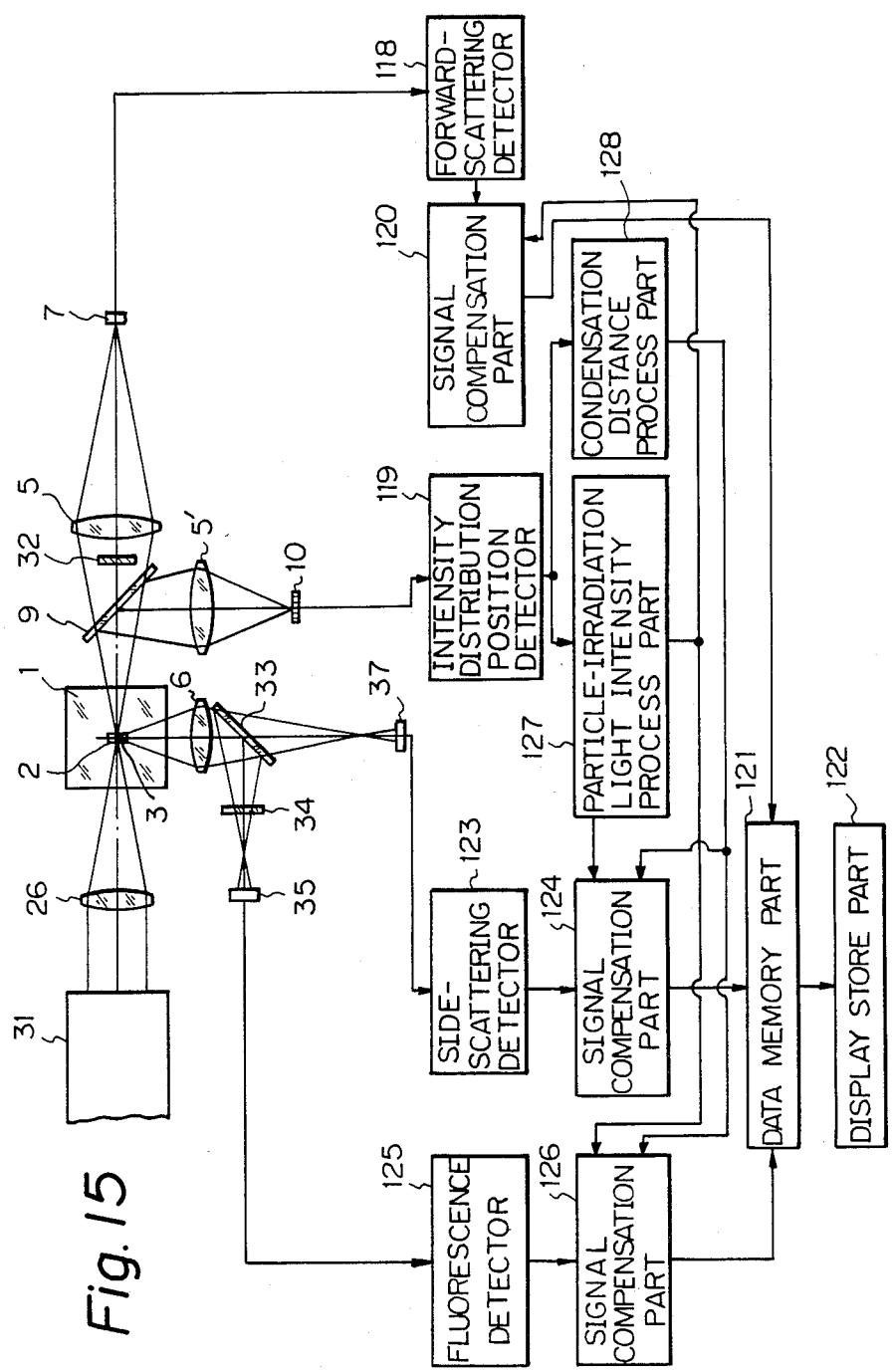

PARTICLE ANALYZING APPARATUS

BACKGROUND OF THE INVENTION

1. Field of the Invention

This invention relates to a particle analyzing apparatus, and in particular to a so-called flow cytometer for applying laser light to a cell-suspended solution flowing at a high speed, detecting the scattered light or fluorescent light by the cellular particle and analyzing the property and structure of the cellular particle.

2. Description of the Prior Art

As shown in FIGS. 1 and 2 of the accompanying drawings, in a flow cytometer, a cell-suspended solution is made to flow to a flow section 2 of minute rectangular cross-section (e.g. 70 μm × 20 μm) in a flow cell 1 with the sheath liquid around said solution, and is hydrodynamically converged at a predetermined location 3, and an irradiation light 4 entering thereinto is also optically converged at said location.

A light receiving system 5 to 8 for forward scattered light and side scattered light or fluorescent light is fixedly provided on the assumption that said converging location does not fluctuate with time. Reference numerals 5 and 6 designate lenses, and reference numerals 7 and 8 denote photodetectors. However, the hydrodynamic converging location has a high possibility of fluctuating with time and, when the hydrodynamic converging location, i.e., the position of a particle to be examined, is displaced in a direction orthogonal to the direction of incidence of the laser, i.e., the vertical direction in FIG. 2, there occur the following problems. The intensity of the laser light strictly has a Gaussian distribution in a direction orthogonal to the direction of incidence of the laser as shown in FIG. 3 of the accompanying drawings and therefore, when the hydrodynamic converging location is displaced as indicated by a–c in the direction orthogonal to the direction of incidence of the laser, the light reception output of the side scattered light or the fluorescent light and further the light reception output of the forward scattered light are varied. If an attempt is made to flatten the intensity distribution of the irradiation light applied to the particle to be examined in order to eliminate this problem, the density of condensing energy will be reduced and an increase in the power of the light source will become necessary.

On the other hand, the center axis of the laser beam may sometimes be displaced relative to the particle to be examined in a direction perpendicular to the direction of application and again in such case, said light reception outputs are varied and therefore, accurate analysis of the particle cannot be accomplished.

Further, displacement of the particle to be examined causes the condensation distance of the light receiving optical system to be varied and thus, the variations in the light reception outputs based thereon must be taken into consideration. Furthermore, any variation in the intensity of the laser light illuminating the particle to be examined must be taken into consideration.

SUMMARY OF THE INVENTION

It is an object of the present invention to provide a particle analyzing apparatus in which any variation in the relative position of the irradiation light beam of an irradiating system for irradiating a particle to be examined and the particle to be examined does not affect the analytical measurement of the particle.

It is also an object of the present invention to provide a particle analyzing apparatus in which the particle to be examined is displaced to vary the condensation distance of a light receiving optical system, whereby the measurement is not affected.

It is a further object of the present invention to provide a particle analyzing apparatus in which any variation in the intensity of a laser light irradiating the particle to be examined does not affect the measurement.

BRIEF DESCRIPTION OF THE DRAWINGS

FIG. 13 illustrates a system for taking out scattered light and fluorscent light sideways.

FIGS. 14A–14C show the factors of the variation in the light reception output.

FIG. 15 shows another embodiment of the present invention.

DESCRIPTION OF THE PREFERRED EMBODIMENTS

Figure 4:
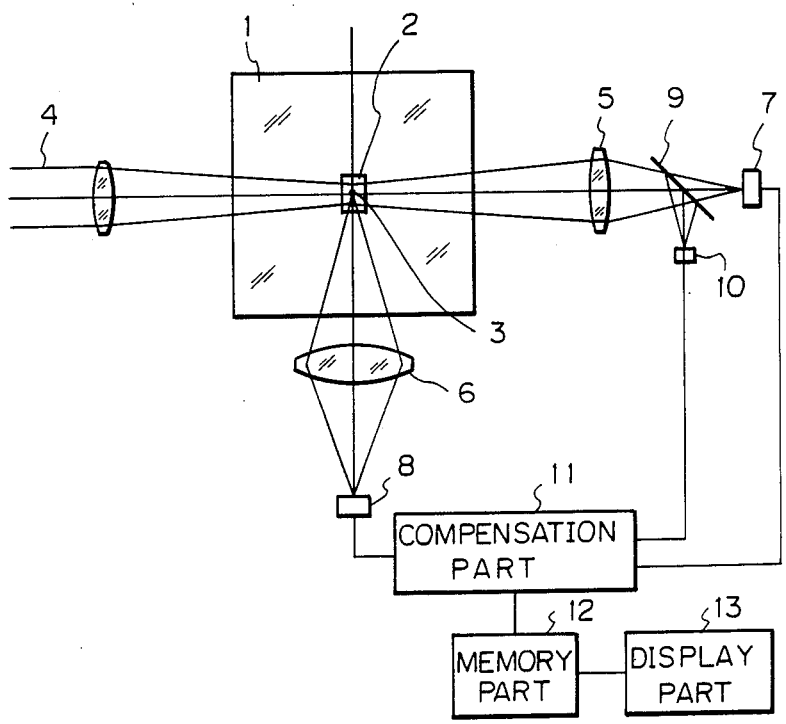
FIG. 4 shows an embodiment of the present invention.

FIG. 4 shows an embodiment of the present invention. In FIG. 4, reference numerals similar to those already referred to designate similar members.

Now, in FIG. 4, forward scattered light is divided by a beam splitter 9 and enters a position detector 10, which detects the positional deviation of the hydrodynamic converged position, i.e., the positional deviation of a particle to be examined. As will later be described, the center of the position detector 10 is set in advance to the position of the center of the incident laser and the hydrodynamic converged position is detected as a position in which the output is minimum, and the amount of positional deviation of this converged position from the laser incidence center is found.

In the present embodiment, the light reception output of side scattered light or fluorescent light, and further, the light reception output of forward scattered light are corrected in accordance with the detected amount of positional deviation.

Figure 5:
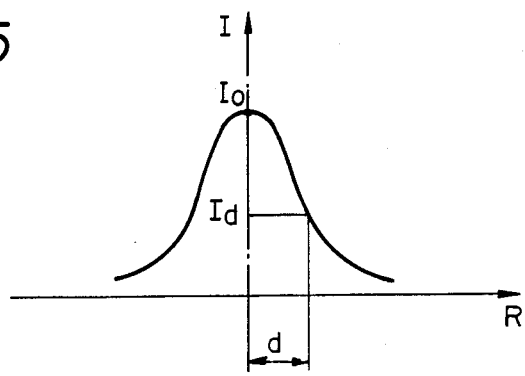
FIG. 5 shows the intensity distribution of the scattered light on the light receiving surface of a photodetector.

As previously described, the intensity of light impinging on the particle varies in the fashion of Gaussian distribution by the hydrodynamic converged position, i.e., the position of the particle and therefore, the scattered light detection signals obtained from photodetectors 7 and 8 also vary in the fashion of a Gaussian distribution as shown in FIG. 5.

When the scattered light reception output obtained when the particle is in its original position is Io and the scattered light reception output obtained when the particle deviates from said position by d in a direction orthogonal to the laser incidence direction Id, if correction is effected by multiplying Id by a coefficient Io/Id, particle analysis which is not affected by displacement can be accomplished. This Io/Id is a value which can be pre-known from the Gaussian distribution as shown in FIG. 5. In the case of side scattered light or fluorescent light, unlike forward scattered light, the intensity of light is weak and therefore, the numerical aperture of the light receiving lens is great and thus, the depth of focus thereof is shallow, and where the intensity of laser light is constant, Id may be further multiplied by a coefficient for correcting the variation in the light reception output when the particle deviates in a direction orthogonal to the direction of incidence of the laser. The output correction based on the variation in the condensation distance of this light receiving optical system will later be described in detail.

Figure 1:
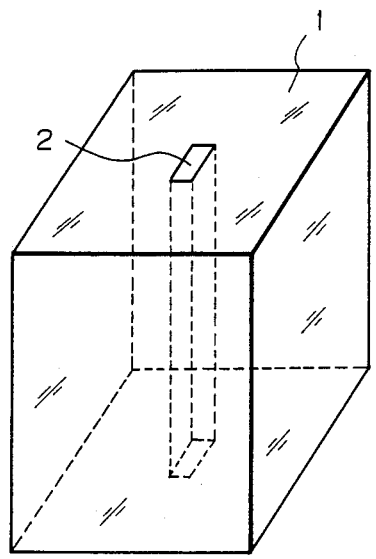
FIG. 1 is a pictorial view of a flow cell.
Figure 2:
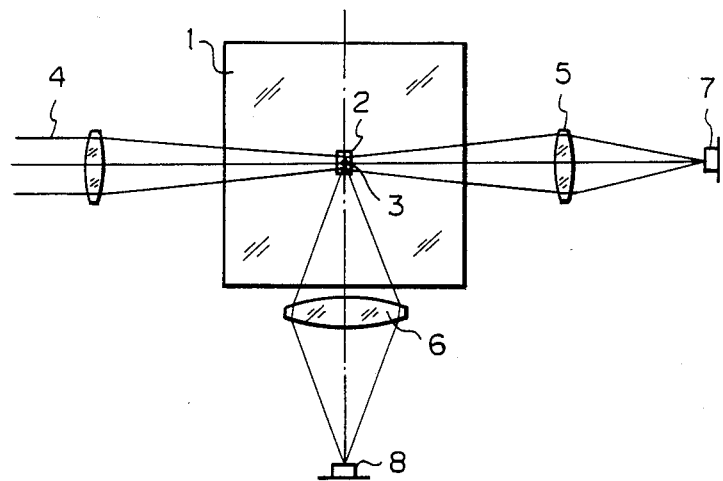
FIG. 2 illustrates an example of the prior art.
Figure 3:
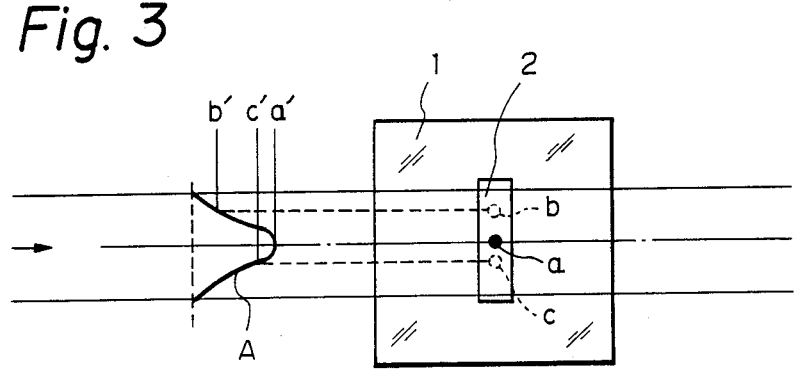
FIG. 3 shows the relation between the particle to be examined in the flow section and the intensity distribution of the laser light.
Figure 6:
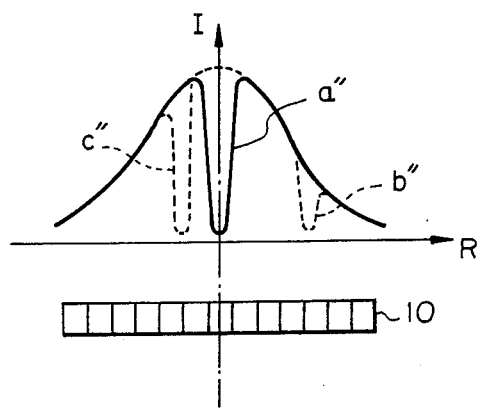
FIG. 6 shows the wave form of a signal obtained from a position detector.

Now, the position detector 10 is a photosensor such as a CCD and is disposed so that if the particle lies at the center of the flow section, the image thereof is formed just at the center of the position detector 10 and therefore, the light intensity distribution on the position detector 10 is such as indicated by a solid line in FIG. 6. In FIG. 6, a" designates the light detection signal when the particle is at a position as in FIG. 3, namely, the center of the flow section, and b" and c" denote the light detection signals when the particle is at positions b and c, respectively, in FIG. 3.

Since the light detection signal is of a minimum output at the position of the particle, the deviation of the position of the particle can be detected. Turning back to FIG. 4, reference numeral 11 designates a compensation part and in this compensation part 11, the data of the photodetectors 7 and 8 are corrected in accordance with the position of the particle and successively stored in a memory part 12.

The stored data are finally displayed, for example, as a histogram data on a display part 13.

While in the above-described embodiment, the beam splitter 9 is provided between the lens 5 in the optical path and the photodetector 7, it may be provided between the flow cell 1 and the lens 5. In this case, an opening for receiving the forward scattered light may be provided between the beam splitter 9 and the lens 5 and it will become possible to change the angles of view of the lights received by the photodetector 7 and the position detector 10.

Figure 7:
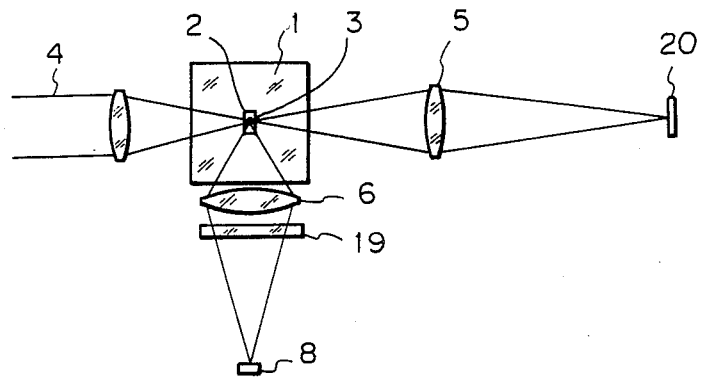
FIGS. 7 and 8 are a major portion construction view and a block diagram, respectively, of a modification in which a photodetector is used also as a position detector.
Figure 8:
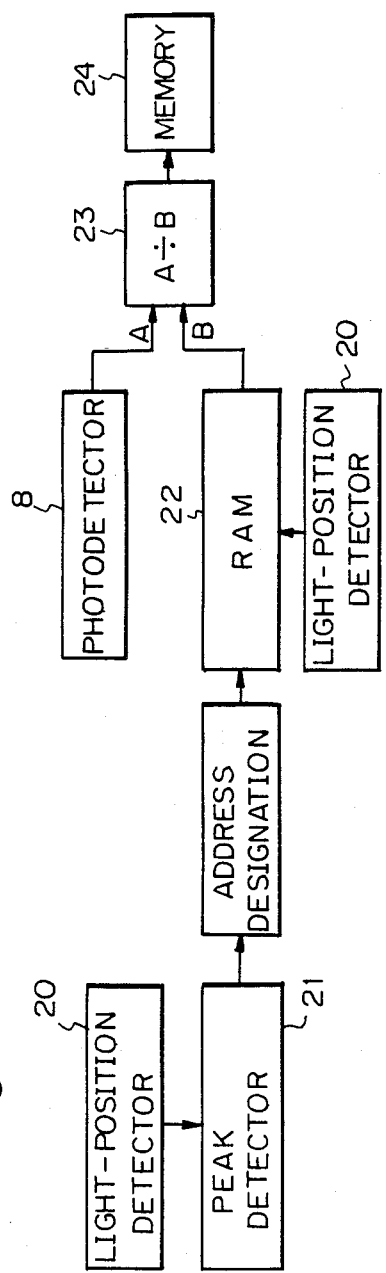

Reference is now had to FIGS. 7 and 8 to describe a modification in which the photodetector 7 and the position detector 10 are provided by a common photodetector. An example in which the measurement of fluorescent light at the side is effected is shown in these Figures. In FIGS. 7 and 8, reference numerals similar to those in FIG. 4 designate similar members.

In FIG. 7, the particle at the hydrodynamic converged position 3 is provided with a particular fluorescent mark, and when irradiation light 4 is applied thereto, the light is photoelectrically converted by a photodetector 8 (generally a photomultiplier detector) via a lens 6 and a barrier filter 19. The barrier filter 19 is a wavelength selecting filter which passes therethrough light of a wavelength in the vicinity of the wavelength of fluorescent light.

On the other hand, as regards the forward scattered light, the so-called O-order light is intercepted by a light-intercepting plate, not shown, provided in the optical path and a component deviating from this light-intercepting plate and entering the lens 5 is integrated and detected on a light-position detector 20. A field stop of a size corresponding to the flow cell may preferably be provided immediately forward of the light-position detector 20.

Now, as previously described, the intensity of an applied beam usually has a Gaussian distribution, and before the article is flowed to the flow section, and more specifically, immediately before the measurement, this distribution is detected by the light-position detector 20 through the lens 5 and stored in a random access type memory element (hereinafter referred to as the RAM).

When the particle is then flowed to the flow section and the measurement is started, the output of the position on the light-position detector 20 which corresponds to the position of the particle becomes minimum as shown in FIG. 6, and the position of the particle is detected therefrom.

When the position of the particle is detected, the light reception outputs of the fluorescent light and the forward scattered light, namely, the outputs of the photodetector 8 and the light-position detector 20, are corrected on the basis of the light intensity distribution of the irradiation light stored in the RAM.

In the present embodiment, the light-position detector 20 is provided with the function of detecting the intensity distribution of the irradiation light and the function of detecting the position of the particle and detecting the forward scattered light differently in time. This will hereinafter be described with reference to a block diagram shown in FIG. 8.

In FIG. 8, the intensity distribution of the irradiation light on the light-position detector 20 is first stored in the RAM 22 before the measurement. Subsequently, the particle to be examined is made to flow and photometering is effected, and the position of the particle on the light-position detector 20 is detected by a peak detector 21. The peak detector 21 detects the position of the particle on the basis of the fact that the light reception output becomes minimum at the position of the particle.

When the position of the particle is detected, the address of the RAM 22 is designated in accordance therewith. This designated content B of the RAM enters the output A of the photodetector 8 as a compensation coefficient and an operation of $A \div B$ is effected in a compensation part 23 and stored in a memory 24. This stored information is displayed on a display device such as ORT with the quantity of fluorescent light as the abscissa and the frequency as the ordinate, whereby a histogram of the particle is obtained and useful particle analysis can be accomplished.

In the above-described embodiment, correction is imparted to the side scattered light, but of course, correction can be imparted to the forward scattered light which is important to analyze the information of the shape (the size or the like) of the particle. It is desirable to rewrite and renew the content of the RAM during each measurement.

Figure 9:
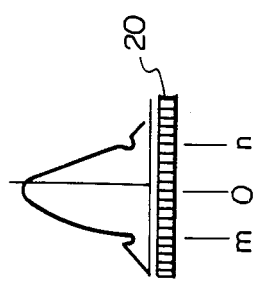
FIG. 9 shows a modification in which the alignment state is further detected.

FIG. 9 shows a modification in which when the illumination distribution of the irradiation light is to be detected by the light-position detector 20, the alignment state is further detected and when the alignment is not good, a warning display is effected. That is, when the positions m and n of the opposite side wall surfaces of the flow cell are detected by the light intensity distribution as shown in FIG. 9, where the intermediate position between the positions m and n on the light-position detector is outside a predetermined range from a predetermined reference position 0, it is judged as bad alignment and a warning display is effected. This is effective in inspecting the alignment state as when the flow cell has been interchanged. If the aforementioned field stop of a size corresponding to the size of the flow cell is provided immediately forwardly of the light-position detector 20, the positions m and n of the opposite side wall surfaces will become clear.

Now, the embodiment already described is for causing the intensity distribution of the irradiation light before the measurement to be stored, but a beam splitter may be disposed in the optical path between the irradiation light source and the flow cell so that the irradiation light may be partly branched off, and a light-position detector may be provided in the branched-off optical path so that the intensity distribution of the irradiation light being measured may be detected.

Figure 10:
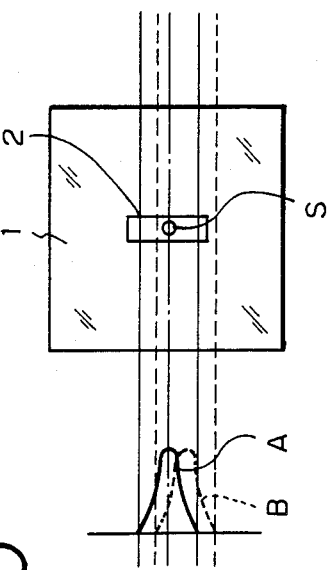
FIG. 10 illustrates a case where the irradiation light beam varies in a direction penpendicular to the direction of application relative to the particle to be examined.
Figure 11:
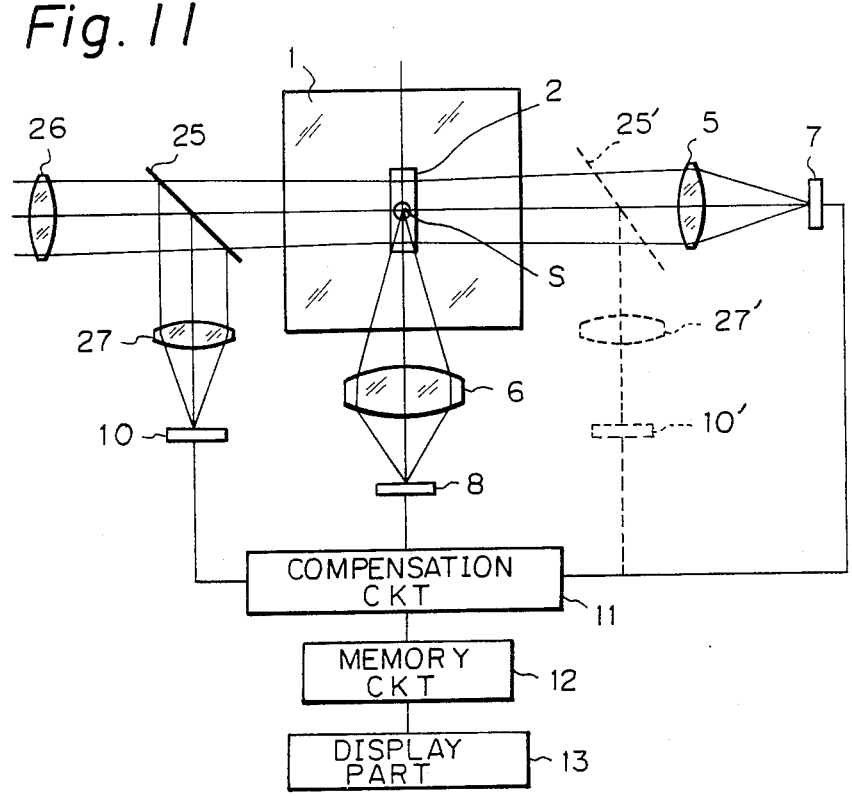
FIG. 11 shows an embodiment in which the light reception output is corrected when the irradiation light beam varies as shown in FIG. 10.
Figure 12:
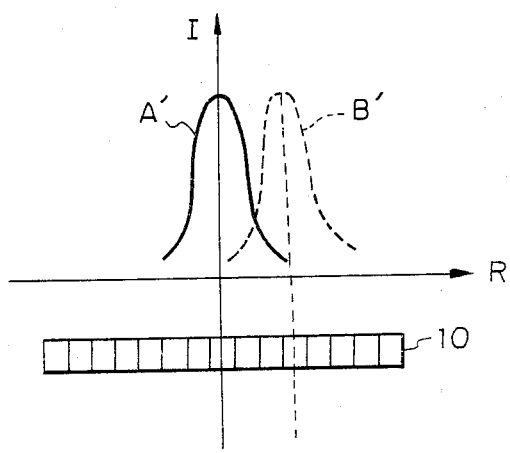
FIG. 12 shows the wave form of the signal of the position detector.

FIG. 11 shows an embodiment in which the light reception output is corrected when, relative to the particle to be examined, the irradiation light beam varies in a direction perpendicular to the direction of application as shown in FIG. 10. In FIG. 10, letter S designates the particle to be examined, letter A denotes the light intensity distribution of a standard irradiation light beam, and letter B designates the light intensity distribution when the irradiation light beam varies perpendicularly to the direction of application. In FIG. 11, the forward scattered light by the particle S to be examined is detected by a lens 5 and a photodetector 7 and the side scattered light is detected by a lens 6 and a photodetector 8, and both of the two detection outputs are input to a compensation circuit 11. On the other hand, the irradiation light is divided by a beam splitter 25 and, as shown in FIG. 12, the light intensity distribution positionally deviated from the central portion of the flow section 2 at the center of the laser beam is detected as the deviation of the output peak position in a position detector 10 through a lens 27, and the measured value thereof is input to the compensation circuit 11, which corrects the value obtained from the photodetector 8, and the result is stored in a memory circuit 12 from moment to moment and finally, the information by the normalized forward scattered light and side scattered light is displayed as a histogram data on a display part 13. Any variation in the light intensity of the laser beam can be detected by the position detector 10 and the outputs of the photodetectors 7 and 8 can be corrected in accordance with the variation in this light intensity.

Besides the above-described embodiment, it is also possible to take out the light entering, for example, the position detector 10 from the front of a lens 26. Also, the particle S to be examined may sometimes deviate more or less relative to the center of the laser light and therefore, it is also possible to effect the detection of the position of the laser light and the detection of the position of the particle S to be examined at a time and correct the detection signal of the scattered light by both position detection signals. If this is done, a more accurate measured value can be obtained. This may be accomplished by providing, for example, a beam splitter 25′, a lens 27′ and a position detector 10′ as indicated by broken lines in FIG. 11, detecting the position of the particle S to be examined by the position detector 10′ and inputting the output thereof to the compensation circuit 11.

Description will now be made of an embodiment in which the light reception output is corrected so that the variation in the condensation distance of the light receiving optical system may not affect the measurement, but before that, description will be made of the influence of the variation in the condensing distance of the light receiving optical system upon the measurement. Here, a system takes out the scattered light and fluorescent light sideways. In FIG. 13, the particle S to be examined wrapped in floating liquid is stably flowing in the flow cell 1 substantially at the center of the flow section 2 thereof by the use of the hydrodynamic focusing method.

The light from a laser light source 31 is condensed on the particle S to be examined by a lens 26. Usually, the intensity of the forward scattered light is detected by a detecting system comprising a stopper 32, a lens 5 and a photodetector 7 and information on the size of the particle S to be examined is obtained.

Also, the particle S to be examined is dyed in fluorescent light and in order to know the cellular chemical property thereof, the intensity of the fluorescent light is detected by an optical system comprising a lens 6, a dichroic mirror 33, a barrier filter 34 and a photodetector 35. Further, in order to know the particulate property in the flow cell, the side scattering in the direction of 90° with respect to the irradiation light is picked up, and the optical system for this is comprised of the lens 6, the dichroic mirror 33, a total reflection mirror 36 and a photodetector 37.

Now, where such photometering is effected, the reduction in photometering accuracy is conceivable in the following points.

First, in FIG. 14A, when the particle S to be examined flowing through the central portion of the flow section 2 of the flow cell 1 has moved in the flow section in the direction of the optic axis of the lens 6 which is perpendicular to the direction of application, the solid angle $\Omega = 2\pi(1 - \omega/2)$ varies and therefore, particularly in the case of a condensing lens of great NA (numerical aperture), the light reception output of the photodetector 35 or 37 fluctuates. This naturally results in a reduction in the accuracy with which the property of the particle to be examined is detected. What has been described above is the influence of the variation in the condensation distance of the light receiving optical system upon measurement.

Now, as shown in FIGS. 14B and 14C, the intensity distribution of the irradiation light in the direction of 90° with respect to the direction of application relative to the flow section 2 usually assumes a Gaussian shape as indicated by 40 and 42, but light intensities impinging on the particles 39, 39′ and 39″ to be examined in accordance with the positions $a_0$, $a_1$ and $a_2$ of the flow section 2 are 1.0, $S_1$ and $S_2$, respectively, and therefore, by the particles moving in the flow section, the accuracy of the detection signal is affected.

Further, when the particle 41 to be examined is flowing through the central portion $b_0$ of the flow section 2 as shown in FIG. 14C, and when the peak has shifted to a position b₁ as indicated by the irradiation light intensity distribution 42, the light intensity changes from 1.0 to t₁, whereby the accuracy of the detection signal is affected as previously described.

Actually, the errors shown in FIGS. 14A, 14B and 14C together cause the reduction in detection accuracy. Furthermore, any variation in the intensity of the irradiation light affects the measurement.

FIG. 15 shows an embodiment in which any relative variation in the irradiation light beam and the position of the particle and any variation in the condensation distance of the light receiving optical system will not affect the measurement.

The apparatus shown in FIG. 15 is basically one in which a half-mirror 9, a lens 5' and a position detector 10 are added to the apparatus shown in FIG. 13, thereby detecting the irradiation light intensity distribution and the position of the particle in the flow section of the flow cell. The position detector 10 may be a CCD or the like as previously mentioned, the position of the particle is detected by detecting a position at which the output is minimum, and the irradiation light intensity distribution is detected from each position output at the point of time whereat the particle is absent.

Said position detector 10 is used for both the detection of the position of the particle and the detection of the irradiation light intensity distribution, but alternatively, the position of the particle and the irradiation light intensity distribution may be detected by discrete detectors.

Now, the output signal from the position detector 10 is detected by an intensity distribution and position detector 119, and the intensity of the light applied to the particle or the distance between the condensing lens 6 and the particle which corresponds to the numerical aperture, i.e., the condensation distance, is operated by a particle-irradiation light intensity process part 127 or a condensation distance process part 128.

The outputs of a fluorescence detector 125 and a side-scattering detector 123 are input to signal compensation parts 126 and 124, respectively, with the outputs of the particle-irradiation light intensity process part 127 and the condensation distance process part 128, and the detection output is corrected and accurate data is obtained.

Also, the output of a forward-scattering detector 118 is input to a signal compensation part 120 with the output of the particle-irradiation light intensity process part 127, and the detection output is corrected and accurate data is obtained.

These data are stored in a data memory part 121 and may be displayed by a display store part 122 as required.

We claim:

1. A particle analyzing apparatus having:
   a flow cell provided with a flow section for passing therethrough a particle to be examined;
   an irradiating system for irradiating the particle to be examined in said flow cell with an irradiation light beam having a light intensity distribution in a direction perpendicular to the direction of irradiation;
   a photodetector for photometering the light from the particle to be examined irradiated by said irradiating system, said photodetector putting out a detection signal;
   deviation information detecting means for detecting information related to the deviation of light intensity of the irradiation light beam of said irradiating system at a position of the particle to be examined, from a reference light intensity of the irradiation light beam at a predetermined position; and
   compensation means for correcting the output of said photodetector in response to the output of said deviation information detecting means.

2. A particle analyzing apparatus according to claim 1, wherein said photodetector is provided with a first photodetector for photometering forward scattered light, and a second photodetector for photometering side scattered light.

3. A particle analyzing apparatus according to claim 2, wherein said deviation information detecting means includes a light intensity distribution detector for detecting the light intensity distribution of said irradiation light beam, and a position detector for detecting a relative position relation of the irradiation light beam and the particle to be examined.

4. A particle analyzing apparatus according to claim 3, wherein said light intensity distribution detector is provided at the side of said photodetector relative to said flow cell.

5. A particle analyzing apparatus according to claim 4, wherein said light intensity distribution detector is provided in an optical path branched off from the optical path to said first photodetector.

6. A particle analyzing apparatus according to claim 4, wherein said light intensity distribution detector is said position detector.

7. A particle analyzing apparatus according to claim 3, wherein said light intensity distribution detector is provided at the side of said irradiating system relative to said flow cell.

8. A particle analyzing apparatus according to claim 7, wherein said light intensity distribution detector is provided in an optical path branched off from the irradiation optical path of said irradiating system.

9. A particle analyzing apparatus according to claim 1, further having a light receiving optical system for receiving the light from the particle to be examined and converging said light on said photodetector, and condensation distance detecting means for detecting condensation distance information regarding said light receiving optical system, and wherein said compensation means corrects the output of said photodetector also on the basis of the output of said condensation distance detecting means.

* * * * *